US011464858B2

(12) United States Patent
Thyagarajan et al.

(10) Patent No.: US 11,464,858 B2
(45) Date of Patent: Oct. 11, 2022

(54) MAGNETIC NANOPARTICLE DELIVERY SYSTEM FOR PAIN THERAPY

(71) Applicant: UNIVERSITY OF WYOMING, Laramie, WY (US)

(72) Inventors: Baskaran Thyagarajan, Laramie, WY (US); Padmamalini Baskaran, Laramie, WY (US)

(73) Assignee: UNIVERSITY OF WYOMING, Laramie, WY (US)

( * ) Notice: Subject to any disclaimer, the term of this patent is extended or adjusted under 35 U.S.C. 154(b) by 0 days.

(21) Appl. No.: 16/448,380

(22) Filed: Jun. 21, 2019

(65) Prior Publication Data

US 2019/0388541 A1 Dec. 26, 2019

Related U.S. Application Data

(60) Provisional application No. 62/689,107, filed on Jun. 23, 2018.

(51) Int. Cl.
| | | |
|---|---|---|
| *A61K 41/00* | (2020.01) | |
| *A61K 9/50* | (2006.01) | |
| *A61K 38/48* | (2006.01) | |
| *A61K 9/51* | (2006.01) | |

(52) U.S. Cl.
CPC .......... *A61K 41/0052* (2013.01); *A61K 9/501* (2013.01); *A61K 9/5031* (2013.01); *A61K 9/5094* (2013.01); *A61K 9/51* (2013.01); *A61K 38/4893* (2013.01)

(58) Field of Classification Search
None
See application file for complete search history.

(56) References Cited

U.S. PATENT DOCUMENTS

| | | | |
|---|---|---|---|
| 3,758,682 A * | 9/1973 | Huber | C12N 9/0089 514/12.2 |
| 9,320,749 B2 | 4/2016 | Thyagarajan et al. | |
| 9,782,481 B2 | 10/2017 | Thyagarajan et al. | |
| 2004/0156852 A1 | 8/2004 | Daum et al. | |
| 2005/0090557 A1 | 4/2005 | Muhammad et al. | |
| 2005/0090732 A1 | 4/2005 | Ivkov et al. | |
| 2005/0271745 A1 | 12/2005 | Gruettner et al. | |
| 2008/0187595 A1 | 8/2008 | Jordan et al. | |
| 2009/0317408 A1 | 12/2009 | Ivkov et al. | |
| 2010/0047180 A1 | 2/2010 | Zeng et al. | |
| 2011/0105825 A1 | 5/2011 | Nayfach-Battilana | |
| 2012/0265001 A1 | 10/2012 | Asmatulu et al. | |

OTHER PUBLICATIONS

Baskaran et al (Preparation and Evaluation of PLGA-Coated Capsaicin Magnetic Nanoparticles. Pharm Res. Jun. 2017;34(6): 1255-1263. Epub Mar. 21, 2017) (Year: 2017).*

Sandrini et al (Botulinum neurotoxin type A for the treatment of pain: not just in migraine and trigeminal neuralgia. The Journal of Headache and Pain (2017) 18:38. p. 1-7). (Year: 2017).*

Vitamin E (https://otcbeautymagazine.com/uses-of-vitamin-e-capsules-or-oil-for-skin-and-hair-2/ (2015) (Year: 2015).*

M Baskaran, B Thyagarajan. "Preparation and Evaluation of PLGA Coated Capsaicin Magnetic Nanoparticles for Target Site Specific Pain Therapeutics." http://www.cell.com/biophysj/pdf/S0006-3495(14)01908-0.pdf, (item 625-Pos) accessed by examiner on Jun. 6, 2017, published on Feb. 8, 2015, 1 printed page.

NK Verma, K Crosbie-Staunton, A Satti, S Gallagher, KB Ryan, T Toddy, C McAtamney, R Macloughlin, P Galvin, CS Burke, Y Volkov, YK Gun'ko. "Magnetic core-shell nanoparticles for drug delivery by nebulization." Journal of Nanobiotechnology, vol. 11:1, 2013, pp. 1-12.

LL Zhang et al. "Activation of Transient Receptor Potential Vanilloid Type-1 Channel Prevents Adipogenesis and Obesity." Circulation Research, vol. 100, 2007, pp. 1063-1070.

A Abushrida. "Formulation of novel polymer coated iron oxide nanoparticles" PhD thesis, University of Nottingham. 2012. pp. i-xxv, 1-268, and two initial pages for 295 printed sheets.

Manuela Tramonlana, et al., Excitatory and inhibitory urinary bladder reflexes induced by stimulation of cervicovaginal capsaicin-sensitive sensory fibers in rats, Naunyn-Schmiedeberg's Arch Pharmacol (2009) 379: pp. 107-114.

Marica Bordicchia, et al., Cardiac nalriurelic peptides act via p38 MAPK to induce the brown fat Ihermogenic program; in mouse and human adipocytes, The Journal of Clinical Investigation, Mar. 2012, vol. 122, No. 3, 15 pp.

Muralidharan Anbalagan, et al., Post-translational modifications of nuclear receptors and human disease, Nuclear; Receptor Signaling (2012) 10, e001, 13 pp.

Rector Arya, et al., Linkage of high-density lipoprolein-cholesterol concentrations to a locus on chromosome 9p in;; Mexican Americans, Nature Genetics, Jan. 2002, vol. 30, 4 pp.

Aexander Bartell, et al, Adipose tissue browning and metabolic health, Nature Reviews Endocrinology. 10.1 (Jan. 2014), 15 pp.

Subal Turdi, et al., Deficiency in AMP-activated protein kinase exaggerates high fat diet-induced cardiac; hypertrophy and contractile dysfunction, Journal of Molecular and Cellular Cardiology 50 (2011) pp. 712-722.

Pengpeng Bi, et al., Inhibition of Notch signaling promotes browning of while adipose tissue and ameliorates obesity,; Nature Medicine, Aug. 2014, vol. 20, No. 8, 10 pp.

Jerel P. Calzo, et al, Development of Muscularity and Weight Concerns in Heterosexual and Sexual Minority Males,; Health Psychol. Jan. 2013 32(1): pp. 42-51.

(Continued)

*Primary Examiner* — Jake M Vu
(74) *Attorney, Agent, or Firm* — Patterson + Sheridan, LLP

(57) ABSTRACT

Embodiments disclosed herein relate to magnetic nanoparticles having a non-narcotic analgesic, as well as methods of preparation and use thereof. A magnetically response pharmaceutical can include a core region having magnetic nanoparticles (MNPs) and a protein-based analgesic. Further, an exterior coating comprising a polymer can be formed around the core region. The magnetically responsive pharmaceutical can be administered to a recipient and directed to a target region using an external magnetic field.

15 Claims, 6 Drawing Sheets

(56) References Cited

OTHER PUBLICATIONS

Lei Cao, et al, While to brown fat phenotypic switch induced by genetic and environmental activation of a; hypothalamic-adipocyte axis, Cell Melab. Sep. 7, 2011; 14(3): pp. 324-338.
Paul Cohen, et al, Ablation of PRDM16 and Beige Adipose Causes Metabolic Dysfunction and a Subcutaneous to; Visceral Fat Switch, Cell Jan. 16, 2014; 156(0), pp. 304-316.
Mark L. Hatzenbuehler, et al., Stigma as a Fundamental Cause of Population Health Inequalities, American Journal of; Public Health, May 2013, vol. 103, No. 5, 9 pp.
Matthijs K.C. Hesselink, et al., Human Uncoupling Protein-3 and Obesity: An Update, Obesity Research, vol. 11, No. 12, Dec. 2003, 15 pp.
Xiaoting Jiang, et al., Inhibition of HDAC3 promotes ligand-independent PPAR activation by protein acetylation, J Mol; Endocrinol. Oct. 2014, 53(2): pp. 191-200.
Ji-Hye Kang, et al., Dietary Capsaicin Reduces Obesity-induced Insulin Resistance and Hepatic Steatosis in Obese; Mice Fed a High-fat Diet, Obesity (2010) 18, pp. 780-787.
Xingxing Kong, et al., IRF4 Is a Key Thermogenic Transcriptional Partner of PGC-1a, Cell 158, Jul. 3, 2014, pp. 69-83.
Daoyan Liu, et al., The Role of Transient Receptor Potential Channels in Metabolic Syndrome, Hypertens Res vol. 31,; No. 11 (2008), 7 pp.
Kinyui Alice Lo, et al., Turning WAT into BAT: a review on regulators controlling the browning of white adipocytes,; Biosci. Rep. (2013) / 33, 9 pp.
Xiaodan Lu, et al., Resistance to Obesity by Repression of VEGF Gene Expression through Induction of Brown-Like; Adipocyte Differentiation, Endocrinology, Jul. 2012, 153(7): pp. 3123-3132.
Jarek Maestu, Visfatin and Adiponectin Levels in Children: Relationships with Physical Activity and Metabolic; Parameters, Cytokines, Growth Mediators and Physical Activity in Children during Puberty. Med Sport Sci. Basel,; Karger, 2010, vol. 55, pp. 56-68.
Nichola J. Marshall, et al., A Role for TRPV1 in Influencing the Onset of Cardiovascular Disease in Obesity,; Hypertension, Jan. 2013, 24 pp.
Derek C Molliver, et al., ASIC3, an acid-sensing ion channel, is expressed in metaboreceptive sensory neurons,; Molecular Pain 2005, 1:35, 13 pp.
Arianne L. Motter, et al., TRPV1-null mice are protected from diet-induced obesity, FEBS Lett. Jun. 25, 2008; 582(15):; pp. 2257-2262.
Haruya Ohno, et al., PPAR agonists induce a white-to-brown fat conversion through stabilization of PRDM16 protein, Cell Metab. Mar. 7, 2012; 15(3): pp. 395-404.
Allessandro Peschechera, et al, "Browning" of adipose tissue—regulation and therapeutic perspectives, Arch Physiol; Biochem, 2013; 119(4): pp. 151-160.
Li Qiang, et al., Brown Remodeling of White Adipose Tissue by SirT1-Dependent Deacetylation of Ppar?, Cell Aug. 3, 2012; 150(3): pp. 620-632.
J. Ren, Leptin and hyperleptinemia—from friend to foe for cardiovascular function, Journal of Endocrinology (2004); 181, pp. 1-10.
Mathan Robbins, et al., Targeting TRPV1 and TRPV2 for potential therapeutic interventions in cardiovascular disease,; Translational Research, Jun. 2013, 8 pp.
Meritxell Rosell, et al, Brown and white adipose tissues: intrinsic differences in gene expression and response to cold; exposure in mice, Am J Physiol Endocrinol Metab 306: 2014, pp. E945-E964.
Patrick Seale, et al, PRDM16 controls a brown fat/skeletal muscle switch, Nature, vol. 454, Aug. 21, 2008, 8 pp.
Maria Servera, et al., Expression of "brown-in-white" adipocyte biomarkers shows gender differences and the influence; of early dietary exposure, Genes Nutr (2014) 9:372, 9 pp.
Irina G. Shabalina, et al, UCP1 in Brite/Beige Adipose Tissue Mitochondria Is Functionally Thermogenic, Cell Reports; 5, Dec. 12, 2013, pp. 1196-1203.

Olivier van Beekum, et al, Posttranslational Modifications of PPAR-y: Fine-tuning the Metabolic Master Regulator,; Obesity (2009) 17, pp. 213-219.
Maarten J. Vosselman, et al., Energy dissipation in brown adipose tissue: From mice to men, Molecular and Cellular; Endocrinology 379 (2013) pp. 43-50.
Andrew J. Whittle, et al, BMP8B Increases Brown Adipose Tissue Thermogenesis through Both Central and; Peripheral Actions, Cell 149, May 11, 2012, pp. 871-885.
Shusuke Yagi, et al., Association of lower limb muscle mass and energy expenditure with visceral fat mass in healthy; men, Diabetology & Metabolic Syndrome 2014, 6:27, 5 pp.
Takeshi Yoneshiro, et al., Transient receptor potential activated brown fat thermogenesis as a target of food; ingredients for obesity management, Curr Opin Clin Nutr Metab Care 2013, 16: pp. 625-631.
Li Li Zhang, et al., Activation of Transient Receptor Potential Vanilloid Type-1 Channel Prevents Adipogenesis and; Obesity, Circulation Research, Apr. 13, 2007, 19 pp.
Claudio J. Villanueva, et al, Adipose subtype-selective recruitment of TLE3 or Prdm16 by PPARy specifies lipid-storage; versus thermogenic gene programs, Cell Metab. Mar. 5, 2013; 17(3): pp. 423-435.
Qi Yu, et al., Expression of TRPV1 in rabbits and consuming hot pepper affects its body weight, Mol Biol Rep (2012); 39: pp. 7583-7589.
Masaki Futamura, et al., Differential effects of topically applied formalin and aromatic compounds on; neurogenicmediated; microvascular leakage in rat skin, Toxicology 255 (2009) pp. 100-106 .
Office Action for U.S. Appl. No. 14/590,124 dated Aug. 3, 2015.
S Chanda, M Bashir, S Babbar, A Koganti, K Bley. "In Vitro Hepatic and Skin Metabolism of Capsaicin." Drug; Metabolism and; Disposition, vol. 36 No. 4, 2008, pp. 670-675.
DL Cioffi. "The Skinny on TRPV1 ." Circulation Research, vol. 100, 2007, pp. 934-936.
Notice of Allowance for U.S. Appl. No. 15/132,488 dated Jun. 15, 2017.
Office Action for U.S. Appl. No. 15/132,488 dated Mar. 13, 2017.
NK Verma et al. "Magnetic core-shell nanoparticles for drug delivery by nebulization." Journal of Nanobiotechnology, vol. 11:1, 2013, pp. 1-12. (Year: 2013).
S Chanda, M Bashir, S Babbar, A Kognanti, K Bley, "In Vitro Hepatic and Skin Metabolism of Capsaicin." Drug Metabolism and Disposition, vol. 36, No. 4, 2008, pp. 670-675. (Year: 2008).
T Ahn, JH Kim, H-M Yang, JW Lee, J-D Kim, "Formation Pathways of Magnetic Nanoparticles by Coprecipitation Method." The Journal of Physical Chemistry C, vol. 116, 2012, pp. 6069-6076. (Year: 2012).
A Akbarzadeh, M Samiei, S Davaran, "Magnetic nanoparticles: preparation, physical properties, and applications in biomedicine." Nanoscale Research Letters, vol. 7:144, 2012, pp. 1-13 (Year: 2012).
Thyagarajan, B, JG Potian, JJ McArdle and P Baskaran. Perturbation to Cholesterol at the Neuromuscular Junction Confers Botulinum Neurotoxin A Sensitivity to Neonatal Mice. Toxicol. Sci. Jun. 22, 2017 Doi:10.1093/toxsci/kfx127.
Padmamalini Baskaran and Baskaran Thyagarajan. Acute and chronic effects of botulinum neurotoxin A in mammalian neuromuscular junction Muscle and Nerve. Nov. 12, 2013. PMID: 24162247.
Baskaran, P, TE Lehmann, E Topchiy, NThirunavukkarasu, S Deshpande, BR Singh and B Thyagarajan. Effects of Enzymatically Inactive Recombinant Botulinum Neurotoxin Type A at the Mouse Neuromuscular Junctions. Toxicon Jun. 25, 2013. pii: S0041-0101(13) 00228-6. PMID:23810945.
Ho, M, LH Chang, M Pires-Alves, B Thyagarajan, JE Bloom, Z Gu, KK Aberle, SA Teymorian, Y Bannai, JJ McArdle and BA Wilson. Recombinant Botulinum Neurotoxin A Heavy Chain-based Delivery Vehicles for Neuronal Cell Targeting. Protein Eng Des Sel. Mar. 2011;24(3):247-53. PMID:21051321.
Potian JG, Vishwendra Patel, JJ McArdle and B Thyagarajan. The inveterate botulinum neurotoxin A ushers in exoendocytic crypts. The Botulinum J. 2010. 1(4). 418-430.

(56) References Cited

OTHER PUBLICATIONS

Thyagarajan, B, JG Potian, CC Garcia, K Hognason, K ?apková, ST Moe, AR Jacobson, KD Janda & JJ McArdle. Effects of hydroxamate metalloendoprotease inhibitors on botulinum neurotoxin A poisoned mouse neuromuscular junctions. Neuropharmacology. Mar. 10, 2010. PMID:20211192.

Thyagarajan, B, N Krivitskaya, K Hognason, JGPotian, CC Garcia and JJ McArdle. Capsaicin protects functions of mouseneuromuscular junctions from the paralytic effects of botulinum neurotoxin A.J. Pharmacol. Exp. Ther. Nov. 2009; 331(2):361-71. PMID: 19654265.

* cited by examiner

MAGNETIC NANOPARTICLE DELIVERY SYSTEM FOR PAIN THERAPY

CROSS-REFERENCE TO RELATED APPLICATION

This application claims benefit of U.S. Provisional Application Ser. No. 62/689,107 filed Jun. 23, 2018, which is herein incorporated by reference in its entirety.

BACKGROUND

Field

Embodiments of the present disclosure generally relate to nanoparticles for controlled drug delivery and methods of using the same.

Description of the Related Art

Pain is an unpleasant sensory and emotional experience associated with actual or potential tissue damage which substantially reduces quality of life. In medical diagnosis, pain is usually viewed as a symptom of an underlying condition. However, in certain instances, pain becomes the disease itself. Due to pain being a complex and subjective phenomenon, defining pain has been a challenge. Generally, pain is classified into either acute or chronic, where acute pain is caused by injury and chronic pain is the condition when pain itself is the disease. Pain may further be classified as either nociceptive or neuropathic. Nociceptive pain is the most common type and results from the detection of noxious stimuli by nociceptors, or specialized peripheral sensory neurons. Neuropathic pain, on the other hand, is associated with direct damage to the neurons.

Analgesics and anesthetics are the primary pharmacologic treatments for all types of pain. The most clinically used drugs are in the opioid family, such as codeine, hydrocodone, morphine, and methadone. However, these drugs have several significant side effects including physical dependence and addiction and are usually only utilized as a last resort for pain management. Other currently available pain therapies, such as nonsteroidal anti-inflammatory drugs (NSAIDS) and acetaminophen, are either inadequate or cause uncomfortable or deleterious side effects with prolonged use. As is the case with many drugs, most pain treatments are not know to localize to a specific region or cell type, and thus require relatively large and sustained doses to achieve long term effects.

Accordingly, what is needed in the art is a pain therapy formulation which can be targeted to specific tissue regions and deliver a sustained release.

SUMMARY

The present disclosure generally relates to a targeted pain therapy formulation and methods of using the same.

In one embodiment, a magnetically responsive pharmaceutical includes a core region having a magnetic nanoparticle (MNP), a non-narcotic analgesic, and an exterior coating formed of a polymer.

In one embodiment, an oral pharmaceutical composition in solid unit dosage form includes between about 1% and about 100% of a magnetically responsive pharmaceutical. The magnetically responsive pharmaceutical has a core region having a magnetic nanoparticle (MNP), a non-narcotic analgesic, and an exterior coating having a biodegradable polymer formed over the MNPs and the non-narcotic analgesic.

In one embodiment, an oral pharmaceutical composition in solid unit dosage form includes between about 1% and about 100% of a magnetically responsive pharmaceutical. The magnetically responsive pharmaceutical includes magnetic nanoparticles (MNPs), a non-narcotic analgesic forming an intermediate layer over the MNPs, and a coating formed of a polymer and surrounding the MNPs and the non-narcotic analgesic. The oral pharmaceutical composition further includes between about 0% to about 99% pharmaceutically-acceptable excipients.

In one embodiment, a magnetically responsive pharmaceutical includes magnetic nanoparticles (MNPs), a non-narcotic analgesic forming an intermediate layer over the MNPs, and an exterior coating formed over the MNPs and the non-narcotic analgesic, the exterior coating further formed of a polymer.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments disclosed herein relate to magnetic nanoparticles which include a non-narcotic analgesic component, as well as methods of preparation and use thereof. A magnetically response pharmaceutical can include a core region having magnetic nanoparticles (MNPs) and a protein-based analgesic. Further, an exterior coating, which is or includes a polymer, can be formed around the core region. The magnetically responsive pharmaceutical can be administered to a recipient and directed to a target region using an external stimulus, for example, a magnetic field.

Protein-based therapies, such as microbial neurotoxins, are becoming more commonly utilized for the treatment of eye problems, muscle stiffness, muscle spasms, migraines, overactive bladder, as well as for cosmetic procedures. Microbial neurotoxins are also a promising group of non-narcotic analgesics for the treatment of pain. Specifically, botulinum toxin type A (BTX-A) has been shown to inhibit pain-associated physical and behavioral responses in mouse model systems as well as human systems. However, the serious side effects associated with the unlocalized diffusion of BTX-A and the uncertainty regarding its mode of action have hindered the development of BTX-A as a therapeutic for pain treatment.

It is believed that BTX-A inhibits pain by decreasing the expression of transient receptor potential vanilloid subfamily 1 proteins (TRPV1), a member of the family of transient receptor potential cation channels expressed on sensory nerve terminals. More specifically, it is believed that BTX-A inhibits pain by suppressing the sensitization of TRPV1 by protein kinase C (PKC). Alternatively, BTX-A may inhibit high frequency firing of voltage-gated sodium channels (VGSC) expressed in nociceptive sensory neurons to decrease pain sensation.

Furthermore, by presenting the non-narcotic and protein-based analgesic as part of a targeted delivery system, the concentration of analgesic available can be sustained over a long period of time while localizing distribution of the drug. By controlling both distribution and available concentration to the target region, undesired side effects can be mitigated while allowing for higher sustained concentrations of the non-narcotic analgesic at the target region. Embodiments are more clearly described with reference to the Figures below.

Figure 1A:
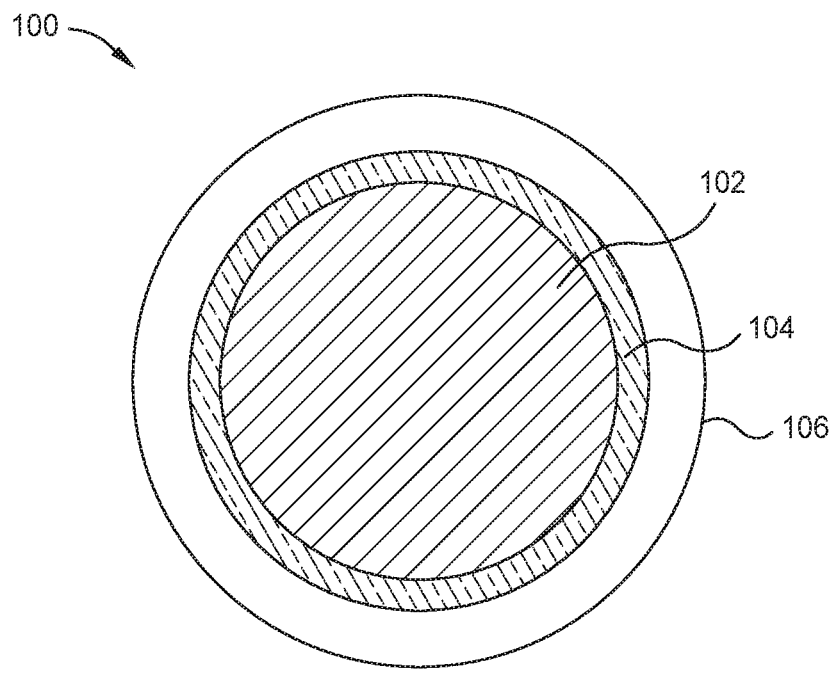
FIG. 1A illustrates a cross-sectional view of a magnetically responsive pharmaceutical according to embodiments described herein.
Figure 1B:
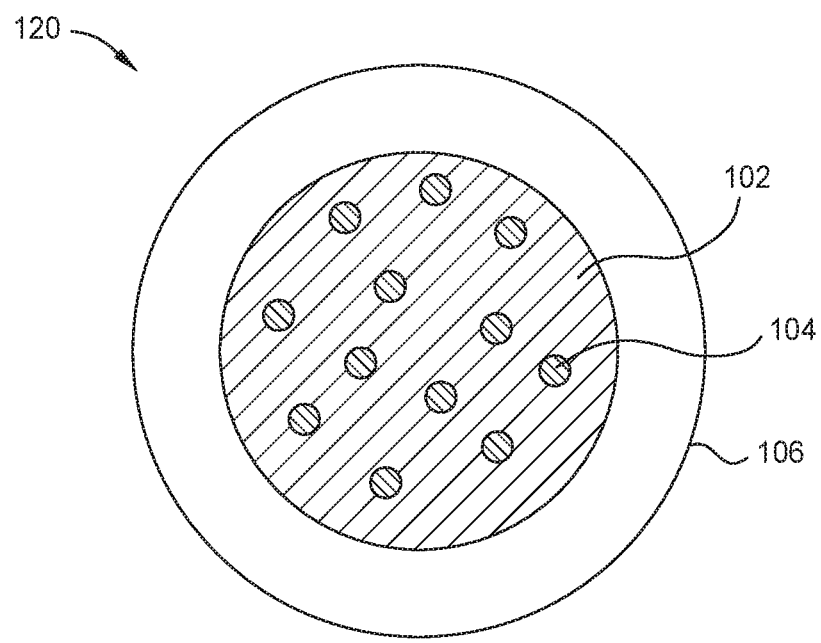
FIG. 1B illustrates a cross-sectional view of a magnetically responsive pharmaceutical according to embodiments described herein.

FIGS. 1A and 1B illustrate cross-sectional views of magnetically responsive particles 100 and 120, according to embodiments described herein. FIG. 1A depicts the magnetically responsive particle 100 having a magnetic nanoparticle (MNP) 102 with an analgesic 104 layer formed around the MNP 102. A polymer 106 coats both the MNP 102 and the analgesic 104. FIG. 1B depicts the magnetically responsive particle 120 with a magnetic nanoparticle (MNP) 102 interspersed with the analgesic 104. The biodegradable polymer 106 coats both the MNP 102 and the analgesic 104.

As used herein, the MNP 102 is a class of nanoparticle which can be manipulated using a magnetic field. Any suitable MNP 102 may be used, including a ferromagnetic MNP 102 such as an iron, nickel, or cobalt-based MNP, and oxides and combinations thereof. In one embodiment, the MNP 102 includes an iron-based nanoparticle, such as an iron oxide nanoparticle. In further embodiments, the iron oxide nanoparticle comprises $Fe^{3+}$ and/or $Fe^{2+}$ ions. In embodiments which use a combination of $Fe^{3+}$ and $Fe^{2+}$ ions, the molar ratio can be between about 3:1 and about 1:1 $Fe^{3+}$ to $Fe^{2+}$ ions, such as about 2:1 of $Fe^{3+}$ to $Fe^{2+}$ ions. Any suitable metal salts can be used for the MNP 102, including but not limited to iron, nickel, and/or cobalt-based salts. For example, suitable iron salts include but are not limited to iron(II) sulfate, iron(II) nitrate, iron(II) chloride, iron(II) perchlorate, iron(III) sulfate, iron(III) nitrate, iron(III) chloride, iron(III) perchlorate, and combinations thereof.

Any suitable method for forming the MNPs 102 can be utilized, including but not limited to co-precipitation, thermal decomposition, microemulsion, flame spray synthesis, and other suitable methods described herein. Though described here in reference to a single MNP 102 for clarity, it is understood that many MNPs 102 are produced in a single cycle using the embodiments described herein.

In one embodiment, ferric chloride and ferrous chloride are dissolved in degassed deionized water. Ammonium hydroxide is then added to the mixture, which results in the mixture having a concentration between about 20% and about 40% ammonium hydroxide. The mixture is then heated to above 50° C., such as about 75° C., followed by cooling to at or below room temperature, such as about 22° C. Optionally, the analgesic 104 can be added to the mixture prior to heating and cooling such that the analgesic 104 co-precipitates with the MNP 102. The MNP 102 is then magnetically filtered and washed with deionized water and neutralized with NaOH.

In one embodiment, the MNP 102 is between about 5 nanometers (nm) and about 30 nm in diameter. In other embodiments, the MNP 102 is between about 5 nm and about 25 nm, between about 5 nm and about 20 nm, between about 2 nm and about 15 nm, between about 5 nm and about 10 nm, between about 7.5 nm and about 30 nm, between about 7.5 nm and about 25 nm, between about 7.5 nm and about 20 nm, between about 7.5 nm and about 15 nm, between about 10 nm and about 30 nm, between about 10 nm and about 25 nm, between about 10 nm and about 20 nm, between about 10 nm and about 15 nm, between about 15 nm and about 30 nm, between about 15 nm and about 25 nm, between about 15 nm and about 20 nm, between about 20 nm and about 30 nm, or between about 20 nm and about 25 nm in diameter.

In one embodiment, the filtered MNP 102 can be suspended in degassed and deionized water. The suspension of the MNP 102 in water is then heated to a temperature of between about 25° C. and about 100° C. for at least 2 minutes, such as a temperature of between about 40° C. and about 75° C. for at least 4 minutes. In one example, the suspension can be heated to about 50° C. in a closed vial for about 5 minutes.

The analgesic 104, such as BTX-A, is then added to the suspension. The analgesic 104 can be at an initial concentration which is limited by the solubility of the analgesic 104 in a buffering agent. Buffering agents include sulfonic acid buffering agents, such as 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), 3-morpholinopropane-1-sulfonic acid, and 3-(N-morpholino)propanesulfonic acid and 3-morpholinopropanesulfonic acid (MOPS). The buffering agent may further include other zwitterionic buffers, such as BIS-TRIS propane, TRIS base, Tricine, or other suitable buffer materials. Though described with reference to BTX-A, it is understood that the analgesic 104 can be any available non-narcotic analgesic, including botulinum toxin type B, capsaicin, capsiate, dihydrocapsaicin, oxytoxin, other capsinoids and capsaicinoids, and combinations thereof. In embodiments where BTX-A is the analgesic 104, BTX-A can be at an initial concentration of between 1 picomolar (pM) and 1 micromolar (µM). In the embodiments described above, the final concentration of BTX-A when added to the suspension is between 10 nanomolar (nM) and 100 nM.

Optionally, the aqueous phase may be decanted and the combination of the MNP 102 and the analgesic 104 may be dried in a rotary evaporator. In the embodiment of FIG. 1A, where the analgesic 104 is added after the precipitation of the MNP 102, the analgesic 104 will predominately form a layer or coating around the MNP 102. In the embodiment of FIG. 1B, where the analgesic 104 is co-precipitated with the MNP 102, the analgesic 104 is interspersed with the MNP 102.

The biodegradable polymer 106 may then be added to the suspension. The biodegradable polymer 106 acts to slow the release of the analgesic 104. The analgesic 104 is released into the local environment at a steady and sustained rate upon degradation of the biodegradable polymer 106. Further, the biodegradable polymer 106 acts to minimize agglomeration of the MNPs 102, leading to improved dispersion of the analgesic throughout the target region.

The biodegradable polymer 106 may be any polymer that is both biodegradable and biocompatible when used with pharmaceuticals. In one embodiment, the biodegradable polymer 106 comprises poly(lactic-co-glycolic acid) (PLGA), polylactic acid (PLA), polyglycolic acid (PGA), poly-D-lactic acid (PDLA), PLGA-dimethacrylate, fluorescent PLGA polymers, Edudragit RL, Edudragit RS, ethyl cellulose, cellulose derivatives, or combinations thereof. In one embodiment, the biodegradable polymer 106 is PLGA. Depending on the ratio of lactide to glycolide used for the polymerization, different forms of PLGA can be obtained. The forms of PLGA are usually identified in regard to the molar ratio of the monomers used (e.g., PLGA 75:25 identifies a copolymer whose composition is 75% lactic acid and 25% glycolic acid). The crystallinity of PLGA can vary from fully amorphous to fully crystalline depending on block structure and molar ratio. PLGA typically shows a glass transition temperature in the range of about 40 degrees Celsius to about 60 degrees Celsius. PLGA can be dissolved by a wide range of solvents, depending on composition. PLGAs having higher lactide compositions can be dissolved using chlorinated solvents such as methylene chloride, whereas PLGAs having higher glycolide compositions can be dissolved with utilization of fluorinated solvents such as hexafluoroisopropanol (HFIP).

PLGA degrades by hydrolysis of its ester linkages in the presence of water. It has been shown that the degradation time PLGA is related to the monomers' ratio used in production, where the higher the content of glycolide units, the lower the degradation time as compared to predominantly lactide materials. In embodiments where the biodegradable polymer 106 is PLGA, the PLGA may be dissolved in a miscibility agent, such as methylene chloride, prior to incorporation in the suspension. The aqueous phase of the suspension, which includes the magnetically responsive particle 100 and/or the magnetically responsive particle 120, can then be decanted. The magnetically responsive particle 100 and/or the magnetically responsive particle 120 can then be dried, such as in a rotary evaporator or vacuum oven.

Surface coating of the MNP 102 with biodegradable polymer 106 layers not only coats the MNP 102, but also attenuate its cluster behavior in aqueous media, resulting in smaller MNP cluster sizes compared to previous MNPs. Reduced cluster size and behavior makes the MNPs 102 more suitable for biomedical applications. Thus, in another embodiment, the MNP 102 comprises an MNP 102 cluster of 250 nm or less in diameter, such as between about 50 nm and about 225 nm in diameter. In some embodiments, the MNP 102 clusters are between about 70 nm and about 200 nm; between about 90 nm and about 200 nm; between about 100 nm and about 200 nm; between about 70 nm and about 180 nm; between about 90 nm and about 180 nm; between about 100 nm and about 180 nm; between about 70 nm and about 150 nm; between about 90 nm and about 150 nm; between about 100 nm and about 150 nm; between about 70 nm and about 120 nm; between about 90 nm and about 120 nm; between about 100 nm and about 120 nm; between about 70 nm and about 100 nm; or between about 90 nm and about 100 nm in diameter.

Any suitable amount of biodegradable polymer 106 can be used to form the magnetically responsive particles 100 and 120, and clusters thereof, of a size suitable for an intended use. In various embodiments, the magnetically responsive particles 100 and 120 comprise a molar ratio of between about 1:40 to 1:300 polymer:metal ion. In further embodiments, the magnetically responsive particles 100 and 120 comprise a molar ratio of between about 1:40 to 1:250; 1:40 to 1:200; 1:40 to 1:150; 1:40 to 1:100; 1:40 to 1:80; 1:80 to 1:300; 1:100 to 1:300; 1:150 to 1:300; 1:200 to 1:300; or 1:250 to 1:300 polymer:metal ion. In still further embodiments, the magnetically responsive particles 100 and 120 comprise a molar ratio of between about 1:1 and 1:10 polymer:metal ion. In other embodiments, the molar ratio of polymer:metal ion is between about 1:2 to about 1:9; about 1:3 to about 1:8; about 1:4 to about 1:7; about 1:5 to about 1:6; or is about 1:1, about 1:2, about 1:3, about 1:4, about 1:5, about 1:6, about 1:7, about 1:8, about 1:9, or about 1:10.

Figure 2:
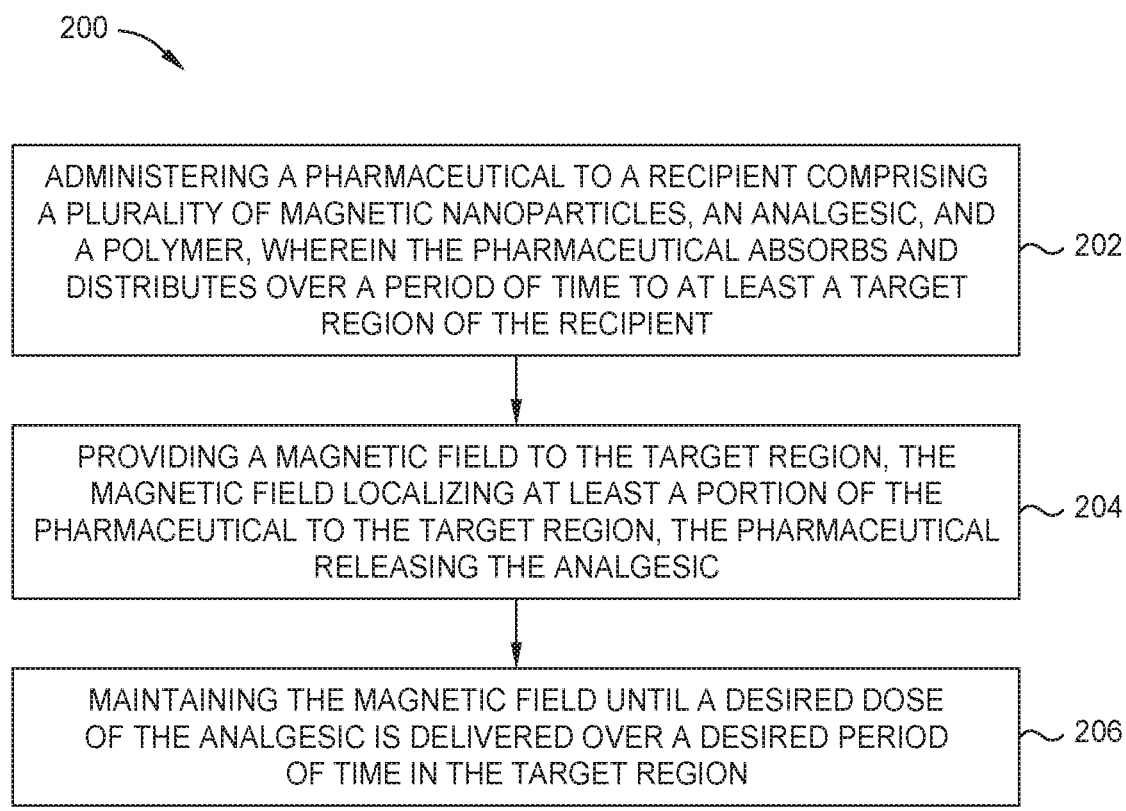
FIG. 2 is a flow diagram of a method of using the magnetically responsive pharmaceutical according to embodiments described herein.
Figure 3A:
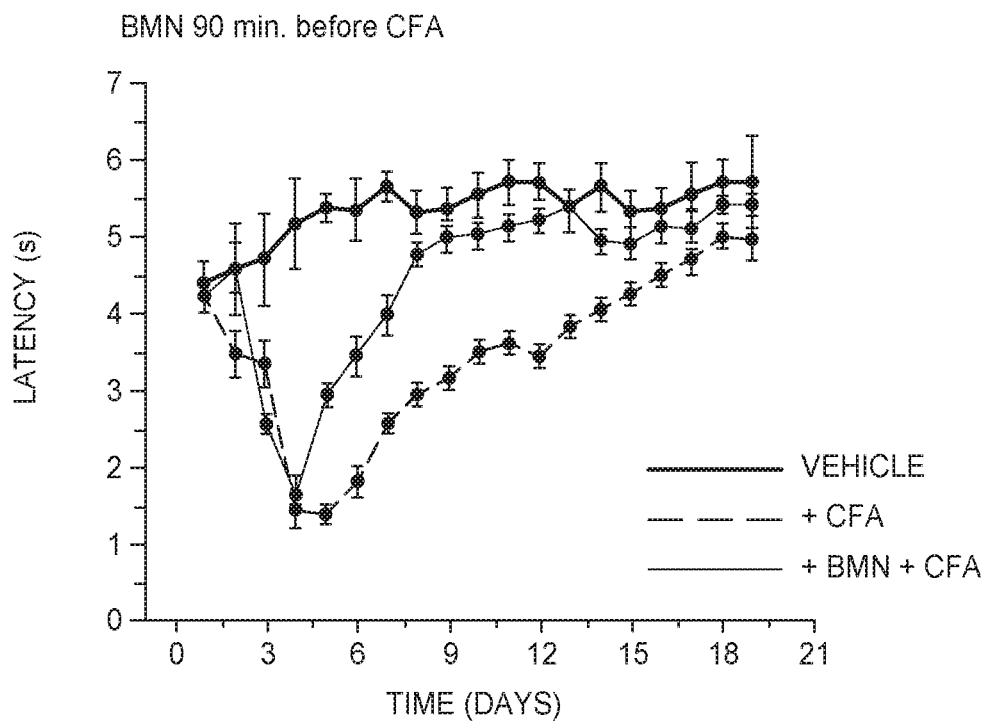
FIG. 3A is a graph depicting the effects of BTX-A-containing magnetically responsive particles on mouse nociceptive behavior according to embodiments described herein.
Figure 3B:
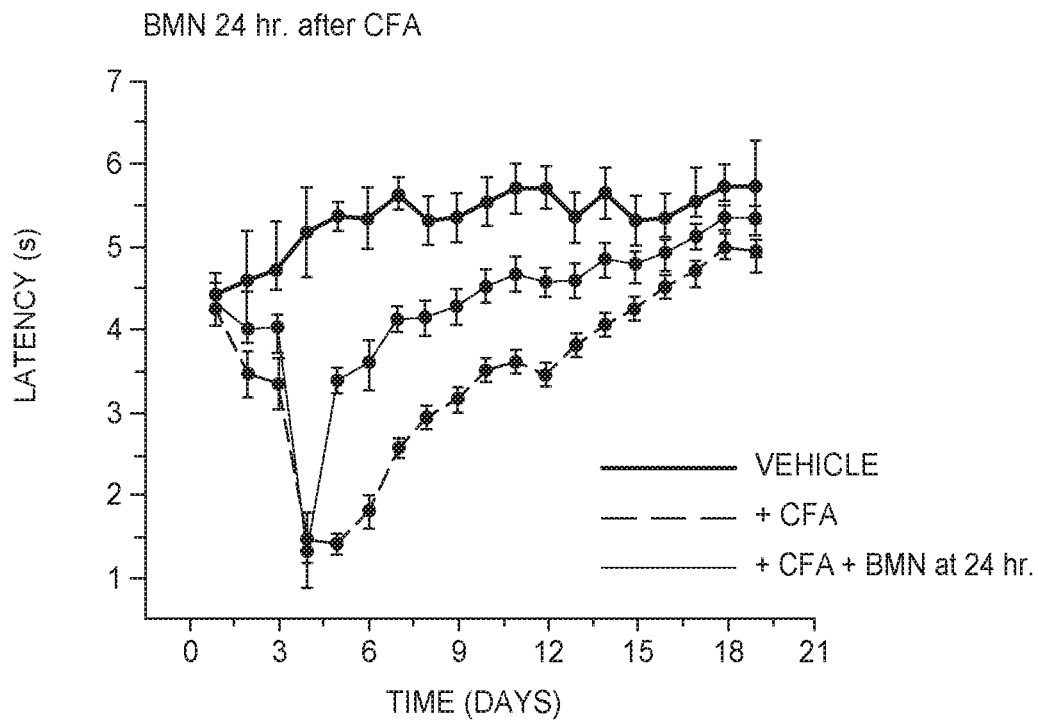
FIG. 3B is a graph depicting the effects of BTX-A-containing magnetically responsive particles on mouse nociceptive behavior according to embodiments described herein.
Figure 4A:
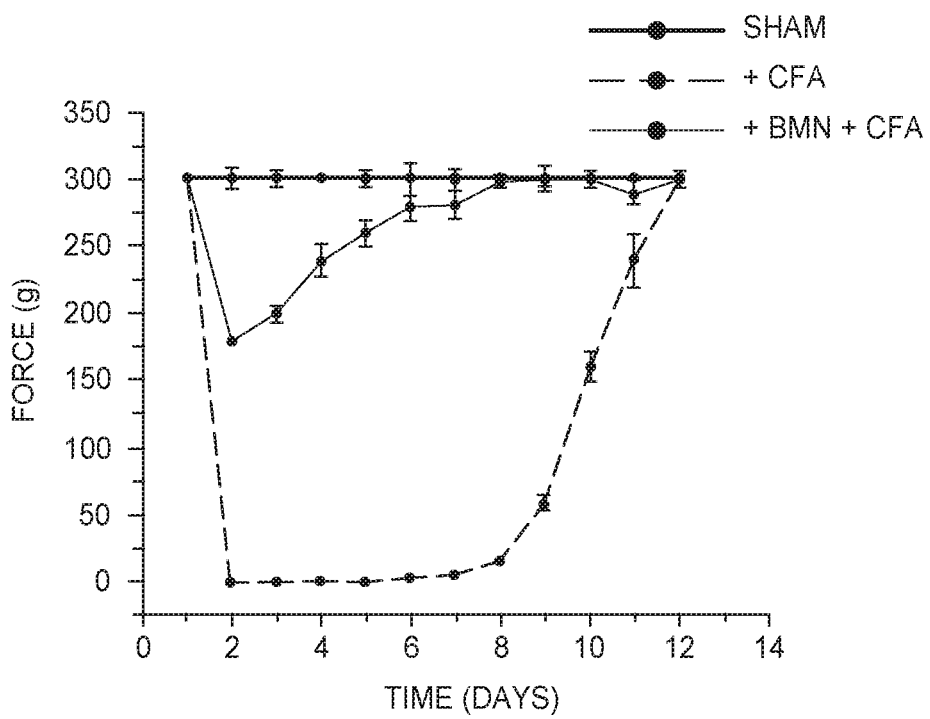
FIG. 4A is a graph depicting the effects of BTX-A-containing magnetically responsive particles on mouse nociceptive behavior according to embodiments described herein.
Figure 4B:
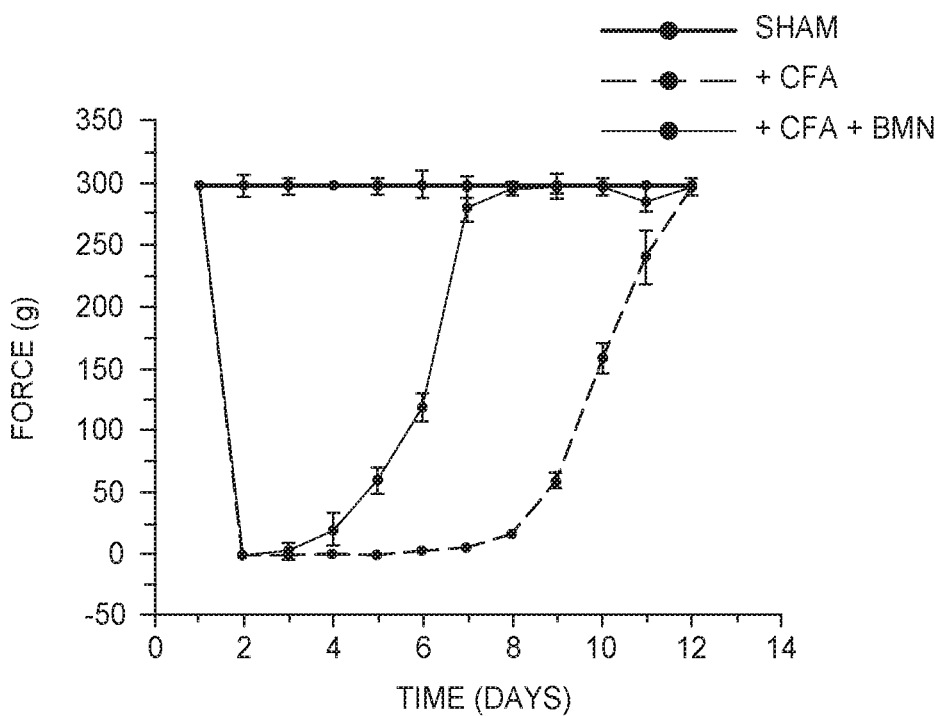
FIG. 4B is a graph depicting the effects of BTX-A-containing magnetically responsive particles on mouse nociceptive behavior according to embodiments described herein.
Figure 5A:
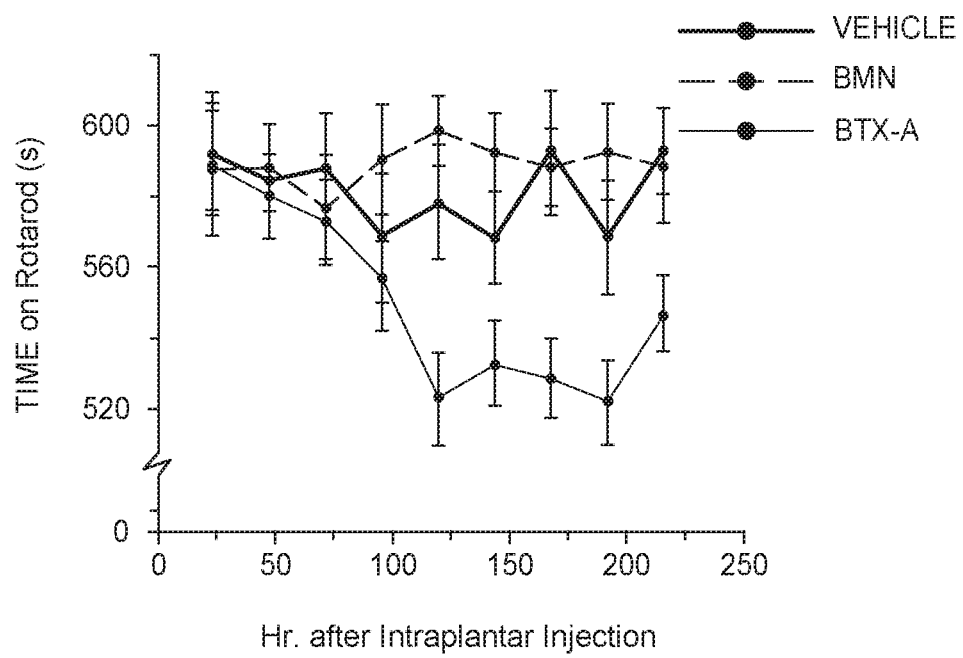
FIG. 5A is a graph depicting the effects of BTX-A-containing magnetically responsive particles on mouse neuromuscular function according to embodiments described herein.
Figure 5B:
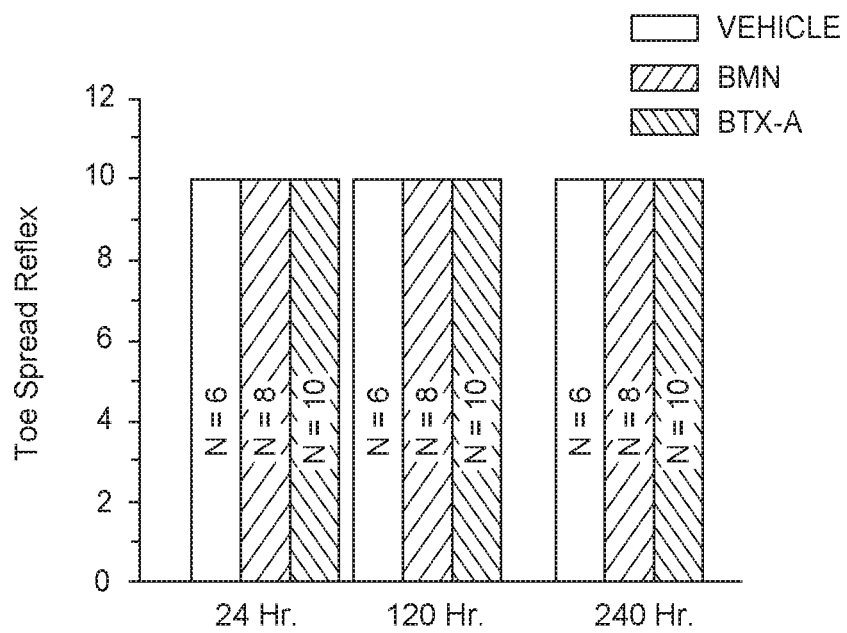
FIG. 5B is a graph depicting the effects of BTX-A-containing magnetically responsive particles on mouse neuromuscular function according to embodiments described herein.
Figure 5C:
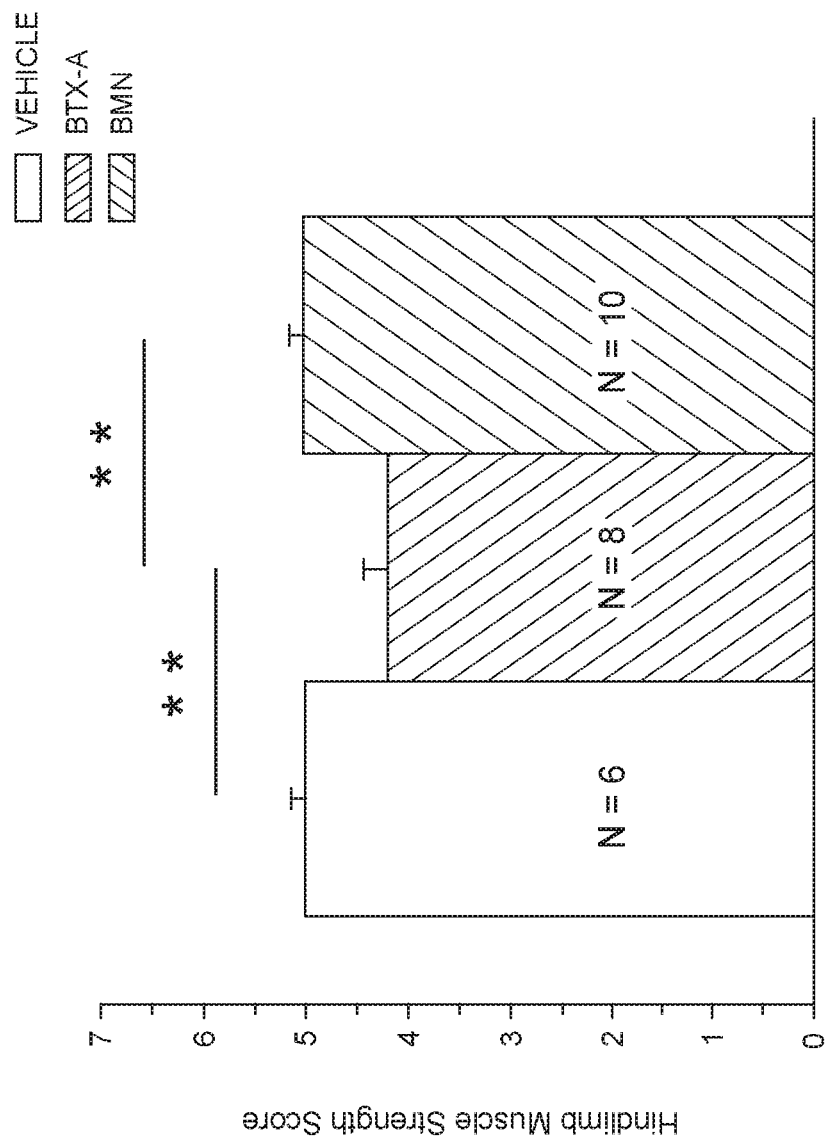
FIG. 5C is a graph depicting the effects of BTX-A-containing magnetically responsive particles on mouse neuromuscular function according to embodiments described herein.

FIG. 2 is a block diagram of a method 200 of using the magnetically responsive particles 100 and 120 described in embodiments herein. The method 200 includes administering a magnetically responsive pharmaceutical to a recipient, such as magnetically responsive particles 100 and 120, wherein the magnetically responsive pharmaceutical absorbs and distributes over a period of time to at least a target region of the recipient at operation 202; providing a magnetic field to the target region, the magnetic field localizing at least a portion of the magnetically responsive pharmaceutical to the target region, the magnetically responsive pharmaceutical releasing the analgesic at operation 204; and maintaining the magnetic field until a desired dose of the analgesic is delivered over a desired period of time in the target region at operation 206.

The method 200 begins by administering the magnetically responsive pharmaceutical to a recipient at operation 202. In all of the embodiments described herein, the magnetically responsive pharmaceutical may be administered parenterally, topically, orally, by inhalation or spray, or rectally (depending on the location and availability of the tissue region) in dosage unit formulations containing conventional non-toxic pharmaceutically acceptable carriers, adjuvants and vehicles. The term parenteral as used herein includes percutaneous, subcutaneous, intradermal, intravascular (e.g., intravenous), intramuscular, intraneural, or intrathecal injection or infusion techniques and the like. In addition, there is provided a pharmaceutical formulation comprising a compound and a pharmaceutically acceptable carrier. The formulations may be in a form suitable for oral use, for example, as tablets, troches, lozenges, aqueous or oily suspensions, dispersible powders or granules, emulsion, hard or soft capsules, or syrups or elixirs.

The magnetically responsive pharmaceutical may be presented in a suitable formulation for an intended delivery route. In some embodiments, the formulation includes gel caps, softgels, and/or capsules. The formulations may be made up in a solid form (including granules, powders or suppositories) or in a liquid form (e.g., emulsions, microemulsions, and nanoemulsions). The formulations of the described embodiments may be applied in a variety of solutions and may be subjected to conventional pharmaceutical operations such as sterilization and/or may contain conventional adjuvants, such as preservatives, stabilizers, wetting agents, emulsifiers, buffers, permeation enhancers, etc.

Formulations intended for oral use may be prepared according to any method known to the art for the manufacture of pharmaceutical compositions and such compositions may contain one or more of sweetening agents, flavoring agents, coloring agents and preservative agents in order to provide palatable preparations. Tablets contain the formulations in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the magnetically responsive pharmaceuticals 100 and 120 are mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for topical and/or transdermal administration may be prepared according to any method known to the art for the manufacture of topical pharmaceutical formulation such as creams, ointments, lotions, thickened lotions, gels, powders, milks, mousse, foams, and sprays. In some embodiments, formulations for topical administration may be in the form of a suspension or dispersion in solvents, such as water or fatty substances, or in the in form of an emulsion or microelmusion. In further embodiments, the emulsions or microemulsions may contain anionic, cationic, nonionic, or amphoteric surfactants. In still further embodiments, the formulations for topical and/or transdermal administration may contain additional penetration enhancers, such as natural, chemical, and biochemical penetration enhancers. For example, the formulations for topical and/or transdermal administration may contain alcohols, polyols, glycerides, amines, amides, cyclodextrines, fatty acids, pyrrolidones, azones, oxizolidinones, sulfoxides, terpenes, essential oils, phospholipids, clofibric acid, and the like.

In one embodiment, a topical pharmaceutical formulation is formed by mixing a desired quantity of magnetically responsive particles 100 and/or 120 with a cream base comprising one or more of cetyl ester wax, white wax, mineral oil, sodium borate, and/or purified water. In one embodiment, the cetyl ester wax, the white wax, and the mineral oil are melted by heating to a temperature about or below 55° C., such as about or below 50° C. The sodium borate and/or purified water are heated to a temperature substantially similar to that used to melt the lipid mixture, such as about or below 55° C., and the aqueous solution is mixed with the lipid mixture to form the cream base. A desired quantity of magnetically responsive particles 100 and/or 120 is mixed into the cream base to form a topical pharmaceutical formulation with a desired concentration of BTX-A. In the embodiments described above, the final concentration of the BTX-A when added to the cream base is between about 1 pM and about 100 pM.

After administration of the magnetically responsive pharmaceutical, the magnetically responsive pharmaceutical absorbs and distributes over a period of time to at least a target region of the recipient. Absorption and distribution is largely dependent on the route of administration and the target region itself. In one example, the target tissue is muscle tissue in the lumbar area of the recipient and the route of administration for the magnetically responsive pharmaceutical is intramuscular injection. In this case, the period of time for absorption and distribution is relatively short, as the magnetically responsive pharmaceutical is provided directly to the target site. In another example, the target tissue is muscle tissue in the lumbar area of the recipient and the route of administration for the magnetically responsive pharmaceutical is transdermal administration. In this case, the period for absorption and distribution includes permeation of the magnetically responsive pharmaceutical through the skin and into the blood stream and travel through the circulatory system until the target site is reached. Application of the magnetic field prior to the drug being available to the target region can lead to mis-accumulation of the magnetically responsive pharmaceutical. Thus, the magnetic field may be applied immediately upon administration or following a period of time thereafter.

At operation 204, a magnetic field is then provided to the target region, the magnetic field localizes at least a portion of the magnetically responsive pharmaceutical to the target region, and the magnetically responsive pharmaceutical releases the BTX-A or other analgesic. The magnetic field may be sourced from either permanent magnets or electromagnets. Further, the magnetic field produced may be continuous or fluctuating. The strength of the magnetic field can vary based on the location of the target site, intervening tissues and other parameters. In one embodiment, a plurality of magnetic fields are used to control the direction and location of the magnetically responsive pharmaceutical. In one example, the magnetic field is between about 0.2 Tesla and about 0.8 Tesla.

The magnetic field may be delivered by any suitable device for positioning of a magnetic field in the proximity of the target region. For example, the magnetic field may be delivered by a permanent magnet disposed in a belt, strap, or brace positioned near the target region. In another example, a fabric may be interwoven with ferromagnetic threads and applied to the epidermis of a recipient. The threads in the fabric may produce a magnetic field of direct a magnetic field from a secondary source, such as an electromagnet coupled to the fabric.

The magnetic field may be applied either over the target region, near the target region or in a position to affect the target region based on known physiology. In some embodiments, the magnetic field is applied over the target region. In this case, a stronger magnetic field may be applied such that the magnetically responsive pharmaceutical is held in position at the target region directly by the magnetic field. In another embodiment, the magnetic field is positioned near the target region and downstream of blood flow, thus slowing the migration of the magnetically responsive pharmaceutical near the target region. Other applications of the magnetic field to control flow of the magnetically responsive pharmaceutical with relation to the target region are contemplated without specific recitation herein.

At operation 206, the magnetic field is maintained until a desired dose of the BTX-A is delivered over a desired period of time in the target region. The dose delivered relates to the dissolution profile of the magnetically responsive pharmaceutical and the period of time that magnetically responsive pharmaceutical is presented to the target region using the magnetic field. The longer that the magnetic field is maintained, the longer that the magnetically responsive pharmaceutical is in range of the target region.

FIGS. 3A-4B are graphs depicting the effects of BTX-A-containing magnetically responsive particles on mouse nociceptive behavior according to embodiments described herein. FIGS. 3A and 4A depict the results of a Hargreaves test for hyperalgesia and a Von Frey test for mechanical allodynia, respectively, in which mice received a single dose of magnetically responsive particles containing BTX-A prior to a dose regiment of complete Freund's adjuvant (CFA). CFA is a nonspecific immune response stimulator commonly used in experimental inflammatory pain models to induce inflammation.

For determination of hyperalgesia, thermal sensitivity of the mice was analyzed by exposing lateral portions of the mice's paws to a radiant heat source. Hind paw withdrawal latency upon exposure to the heat source was monitored and recorded. For allodynia, the mechanical force required to elicit a physical response upon contact with Von Frey filaments was monitored and recorded. Mice were placed in plastic cylinders on a wire mesh and allowed to habituate for 15 minutes prior to testing. Utilizing a Von Frey filament, force was applied to a hind paw five times over a total period of 30 seconds. The procedure was performed on both ipsilateral and contralateral paws, and then repeated with higher force filaments to verify threshold levels.

In these examples, mice received an intraplantar injection of PLGA-coated BTX-A magnetic particles (1 nm, 10 μL) followed by a 90-minute incubation period. After 90 minutes, the mice received an intraplantar injection of CFA (1 mg/ml, 50 μL), which was repeated after a 1-, 2-, and 15-minute time period and then every 24 hours thereafter until recovery. Von Frey filament force and hind paw withdrawal latency were monitored and recorded daily for 30 days and particle safety for 90 days. The force (g) and latency (s) were plotted against time (days) and compared to that of mice injected with only CFA or empty vehicle.

FIGS. 3B and 4B depict the results of a Hargreaves test and a Von Frey test, respectively, in which mice received a single dose of CFA prior to a dose regiment of magnetically responsive particles containing BTX-A. In these examples, mice received an intraplantar injection of CFA (1 mg/ml, 50 μL) followed by a 24-hour incubation period. After 24 hours, the mice received an intraplantar injection of PLGA-coated BTX-A magnetic particles (1 nm, 10 μL) every 24 hours until recovery. Von Frey filament force and hind paw withdrawal latency were monitored and recorded daily for 30 days and particle safety for 90 days. The force (g) and latency (s) were plotted against time (days) and compared to that of mice injected with only CFA or empty vehicle.

As illustrated in FIGS. 3A-4B, mice injected with the PLGA-coated BTX-A magnetic particles (+CFA, +BMNP) exhibited improved CFA-induced pain behavior responses compared to negative control mice (+CFA). Withdrawal latency and Von Frey forces for +CFA, +BMNP mice increased to substantially similar levels as positive control mice (Vehicle) within substantially shorter timeframes than +CFA mice, thus demonstrating the inhibitive effect on hyperalgesia and allodynia by the PLGA-coated BTX-A magnetic particles. In fact, in some instances, behavioral responses of mice injected with BTX-A magnetic particles returned to substantially normal levels in about half the time required for negative control mice. Additionally, no toxicities were observed during these trials, including dysthermia, which is a common effect of TRPV1 antagonists.

FIGS. 5A-5C are graphs depicting the effects of PLGA-coated BTX-A magnetic particles on mouse neuromuscular function according to embodiments described herein. In these examples, mice received an intraplantar injection of the PLGA-coated BTX-A magnetic particles (1 nm or 0.01 nm, 10 μL) and were subjected to various mechanophysiological tests to determine whether the BTX-A containing nanoparticles caused neuromuscular toxicity.

For FIG. 5A, mice were placed on a rotarod apparatus to monitor the effects of the BTX-A magnetic particles on balance, coordination, motor-planning, and grip strength. Prior to testing, the mice were first allowed to adapt to the rotating rod with one week of training. Rotarod performance was then tested biweekly after administration of the PLGA-coated BTX-A magnetic particles and compared to that of mice injected with only empty vehicle (Vehicle) or free BTX-A (BTX-A). The mean duration of time on the rotarod was averaged for three repeated suns separated by 30 minute intervals. As demonstrated by FIG. 5A, the injection of PLGA-coated BTX-A magnetic particles did not affect muscle coordination or performance of the mice on the rotarod apparatus, as mean duration of time on the rotarod for BTX-A-injected mice was similar to that of control mice throughout the experimental period. Mice administered with free BTX-A, however, demonstrated significantly decreased performance within 125 hours of injection.

In FIG. 5B, the toe spread reflex of the mice was scored from 1 to 10 depending on the number of toes that the mouse could extend when lifted by the tail. Toe spreading reflexes remained substantially consistent among BTX-A-injected mice and control mice. Thus, it was demonstrated that injection of PLGA-coated BTX-A magnetic particles containing BTX-A did not cause neuroparalysis or other neuromuscular toxicities that would prevent the mice to extend their toes.

In FIG. 5C, the hind limb muscle strength was scored by evaluating the ability of the mouse to move the legs and grip a rod. A score of 0 meant no movement of the mouse towards the rod; 1, the mouse made movement towards the rod, but profound weakness prevented gripping the rod to support the mouse's body weight; 2, the mouse was able to support its body weight on the rod with a weak grip; 3, the mouse was able to hold onto the rod for at least 30 seconds; 4, the mouse easily reached for and grabbed the rod to support its body weight for at least one minute; 5, the mouse quickly grasped the rod with a strong grip and supported its body weight for at least two minutes. As shown in FIG. 5C, mice injected with free BTX-A experienced difficulty in performing these physical tests, thus indicating that the free BTX-A caused significant muscle weakness. Mice injected with BTX-A magnetic particles, however, were able to move their limbs and grip the rod with similar success to that of positive control mice, demonstrating that the BTX-A magnetic particles did not affect muscle strength.

Thus, the PLGA-coated BTX-A magnetic particles were capable of inhibiting pain-associated physical and behavioral responses without causing deleterious side effects such as muscle weakness, neuroparalysis, and other neuromuscular toxicities. These results suggest that the PLGA-coated BTX-A magnetic particles may be utilized as an effective therapy for site-specific pain treatment.

Described herein are magnetically responsive pharmaceuticals for use in targeted pain therapies, methods of making said pharmaceuticals and methods of using the same. The pharmaceuticals and methods described herein target an analgesic to a specific site in the body. Through this pathway, pharmaceuticals and methods described herein can be utilized to effectively treat acute and chronic pain while exhibiting minimal or no side effects attributed with conventional delivery mechanisms.

While the foregoing is directed to embodiments of the present disclosure, other and further embodiments of the disclosure may be devised without departing from the basic scope thereof, and the scope thereof is determined by the claims that follow.

What is claimed is:

1. A magnetically responsive pharmaceutical for topical administration comprising:
  a core region having:
    a magnetic nanoparticle (MNP); and
    botulinum toxin type A; and
    an exterior coating formed over the MNPs and the botulinum toxin type A, the exterior coating comprising a polymer, wherein the magnetically responsive pharmaceutical for topical administration comprises a molar ratio of polymer to metal ion between 1:40 and 1:300, and a concentration of the botulinum toxin type A between 1 pM and 100 pM.

2. The pharmaceutical of claim 1, wherein the polymer is selected from the group consisting of poly(lactic-co-glycolic acid) (PLGA), Polylactic acid (PLA), Polyglycolic acid (PGA), poly-D-lactic acid (PDLA), PLGA-dimethacrylate, fluorescent PLGA polymers, Poly(ethyl acrylate-co-methyl methacrylate-co-trimethylammonioethyl methacrylate chloride) 1:2:0.2, Poly(ethyl acrylate-co-methyl methacrylate-co-trimethylammonioethyl methacrylate chloride) 1:2:0.1, Ethyl cellulose, and combinations thereof.

3. The pharmaceutical of claim 1, wherein the botulinum toxin type A forms an intermediate layer over the MNPs.

4. The pharmaceutical of claim 1, wherein the MNP is selected from the group consisting of iron, cobalt, nickel, and combinations thereof.

5. A cream-based pharmaceutical composition for topical administration comprising:
  from about 1% to about 100% of a magnetically responsive pharmaceutical, the magnetically responsive pharmaceutical comprising:
    a core region having:
      a magnetic nanoparticle (MNP); and
      botulinum toxin type A; and
      an exterior coating formed over the MNPs and the botulinum toxin type A, the exterior coating comprising a biodegradable polymer, wherein the magnetically responsive pharmaceutical comprises a molar ratio of polymer to metal ion between 1:40 and 1:300, and wherein the cream-based pharmaceutical composition for topical administration comprises a concentration of botulinum toxin type A between 1 pM and 100 pM.

6. The pharmaceutical composition of claim 5, wherein the biodegradable polymer is selected from the group consisting of poly(lactic-co-glycolic acid) (PLGA), Polylactic acid (PLA), Polyglycolic acid (PGA), poly-D-lactic acid (PDLA), PLGA-dimethacrylate, fluorescent PLGA polymers, Poly(ethyl acrylate-co-methyl methacrylate-co-trimethylammonioethyl methacrylate chloride) 1:2:0.2, Poly(ethyl acrylate-co-m ethyl methacrylate-co-trimethylammonioethyl methacrylate chloride) 1:2:0.1, Ethyl cellulose, and combinations thereof.

7. The pharmaceutical composition of claim 5, wherein the botulinum toxin type A forms an intermediate layer over the MNPs.

8. The pharmaceutical composition of claim 5, wherein the magnetic nanoparticle is selected from the group consisting of iron, cobalt, nickel and combinations thereof.

9. A pharmaceutical composition for topical administration comprising:
  a magnetically responsive pharmaceutical, the magnetically responsive pharmaceutical comprising:
    magnetic nanoparticles (MNPs);
    botulinum toxin type A forming an intermediate layer over the MNPs; and
    a coating surrounding the MNPs and the botulinum toxin type A, the coating comprising a polymer; and
  a cream base comprising one or more of cetyl ester wax, white wax, and mineral oil, wherein the magnetically responsive pharmaceutical comprises a molar ratio of polymer to metal ion between 1:40 and 1:300, and wherein the pharmaceutical composition for topical administration comprises a concentration of botulinum toxin type A between 1 pM and 100 pM.

10. The pharmaceutical composition of claim 9, wherein the polymer is selected from the group consisting of poly(lactic-co-glycolic acid) (PLGA), Polylactic acid (PLA), Polyglycolic acid (PGA), poly-D-lactic acid (PDLA), PLGA-dimethacrylate, fluorescent PLGA polymers, Poly(ethyl acrylate-co-methyl methacrylate-co-trimethylammonioethyl methacrylate chloride) 1:2:0.2, Poly(ethyl acrylate-co-methyl methacrylate-co-trimethylammonioethyl methacrylate chloride) 1:2:0.1, ethyl cellulose, and combinations thereof.

11. The pharmaceutical composition of claim 9, wherein the MNPs comprise a material selected from the group consisting of iron, cobalt, nickel and combinations thereof.

12. A magnetically responsive pharmaceutical for topical administration comprising:
  magnetic nanoparticles (MNPs);
  botulinum toxin type A forming an intermediate layer over the MNPs; and
  an exterior coating formed over the MNPs and the botulinum toxin type A, the exterior coating comprising a polymer, wherein the magnetically responsive pharmaceutical for topical administration comprises a molar ratio of polymer to metal ion between 1:40 and 1:300, and a concentration of the botulinum toxin type A between 1 pM and 100 pM.

13. The pharmaceutical of claim 12, wherein the polymer is selected from the group consisting of poly(lactic-co-glycolic acid) (PLGA), Polylactic acid (PLA), Polyglycolic acid (PGA), poly-D-lactic acid (PDLA), PLGA-dimethacrylate, fluorescent PLGA polymers, Poly(ethyl acrylate-co-methyl methacrylate-co-trimethylammonioethyl methacrylate chloride) 1:2:0.2, Poly(ethyl acrylate-co-methyl methacrylate-co-trimethylammonioethyl methacrylate chloride) 1:2:0.1, Ethyl cellulose, and combinations thereof.

14. The pharmaceutical of claim 12, wherein the MNPs comprise a material selected from the group consisting of iron, cobalt, nickel and combinations thereof.

15. A magnetically responsive pharmaceutical for topical administration comprising:
a core having:
a magnetic nanoparticle (MNP); and
botulinum toxin type A; and
an exterior coating formed over the MNPs and the botulinum toxin type A, the exterior coating comprising a polymer, wherein the magnetically responsive pharmaceutical for topical administration comprises a concentration of the botulinum toxin type A between 1 pM and 100 pM.

* * * * *